Figure 1:
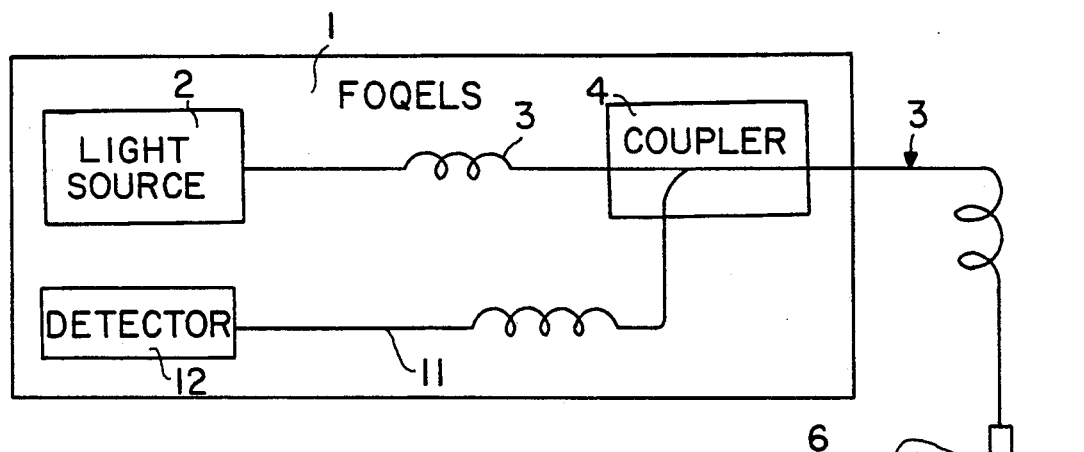
Figure 1A:
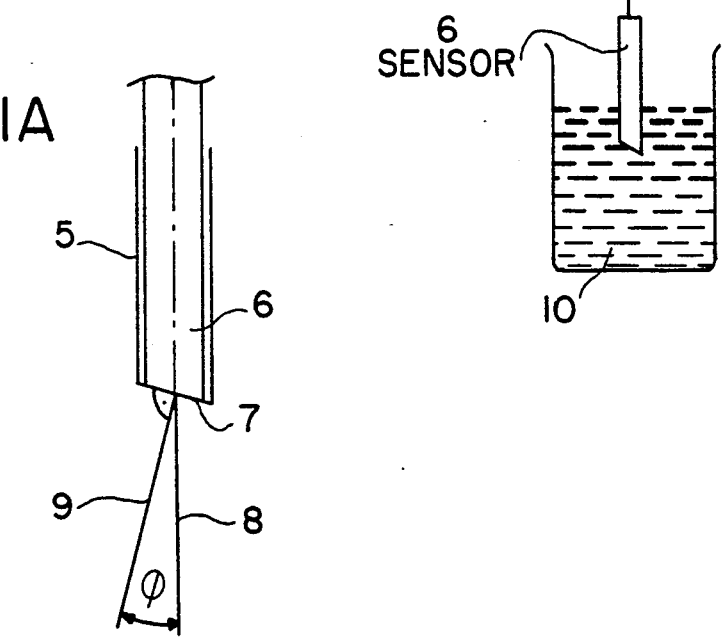

United States Patent [19]

Auweter et al.

[11] Patent Number: 5,011,279
[45] Date of Patent: Apr. 30, 1991

[54] FIBER-OPTICAL SENSOR

[75] Inventors: Helmut Auweter, Limburgerhof; Dieter Horn, Heidelberg; Dieter Lilge; Juergen Wortmann, both of Limburgerhof, all of Fed. Rep. of Germany

[73] Assignee: BASF Aktiengesellschaft, Ludwigshafen, Fed. Rep. of Germany

[21] Appl. No.: 205,353

[22] Filed: Jun. 10, 1988

[30] Foreign Application Priority Data

Jun. 13, 1987 [DE] Fed. Rep. of Germany ....... 3719806

[51] Int. Cl.$^5$ .......................................... G01N 21/00
[52] U.S. Cl. .................. 356/28.5; 350/96.15; 350/337; 350/349
[58] Field of Search ............... 356/5, 28-28.5, 356/337, 349; 350/96.1, 96.15

[56] References Cited

U.S. PATENT DOCUMENTS

| | | | |
|---|---|---|---|
| 4,495,412 | 1/1985 | Thoone et al. | 350/96.1 X |
| 4,585,298 | 4/1986 | Mori | 350/96.1 |
| 4,637,716 | 1/1987 | Auweter et al. | 356/28.5 |
| 4,693,552 | 9/1987 | Jeskey | 350/96.1 X |
| 4,730,883 | 3/1988 | Mori | 350/96.1 |
| 4,740,047 | 4/1988 | Abe et al. | 350/96.1 X |
| 4,793,679 | 12/1988 | Toda et al. | 350/96.1 X |

FOREIGN PATENT DOCUMENTS 0121002  5/1988  Japan .................................. 350/96.1

OTHER PUBLICATIONS

Applied Optics 14 (1975); vol. 14, No. 1; pp. 189-196; "Measurement of the Velocity of Blood Flow Using a F. O. Catheter and Optical Mixing Specroscopy"; Tanaka et al.

Microwaves, Optics and Acoustics (1978); vol. 2, No. 1; pp. 13-18; "The Fibre-Optic Doppler Anemometer", by R. B. Dyott.

Primary Examiner—Stephen C. Buczinski
Assistant Examiner—Bernarr Earl Gregory
Attorney, Agent, or Firm—Keil & Weinkauf

[57] ABSTRACT

In a fiber-optical sensor used for measuring the Doppler broadening of scattered laser light by the principle of quasi-elastic light scattering (QELS), the scattered light originating from particles in movement, the emergence surface (7) for the laser light at the end of a single-mode or multimode light guide (3) used as an immersion probe is inclined at an angle $0 < \phi \leq 15°$, preferably $1° \leq \phi \leq 6°$, the angle of inclination being de-fined by the optical axis (8) of the light guide (3) and the normal (9) of the emergence surface (7).

2 Claims, 5 Drawing Sheets

FIBER-OPTICAL SENSOR

The present invention relates to a fiber-optical sensor for the measuring of the Doppler broadening of scattered Laser Light by the principle of quasi-elastic Light scattering (QELS), the scattered light originating from particles in motion.

A fiber-optical sensor can be used, in conjunction with a suitable optoelectronic measuring apparatus, for two fundamentally different purposes. On the one hand, the fiber-optical sensor is used in velocimetry. Here, flow velocities, velocity gradients and turbulence can be measured even at remote points inaccessible to a direct laser beam. Flows in metal pipes, in combustion engines and in blood streams are but a few examples.

On the other hand, a fiber-optical sensor can be used in physicochemical analysis to determine diffusion coefficients and diameters of dispersed colloidal particles by the methods of photon correlation spectroscopy. A fiber-optical sensor permits these measurements to be carried out in situ, in particular even at points which are not readily accessible, for example reaction vessels or spaces where there is a danger of explosion. Furthermore, a fiber-optical sensor can be used to investigate highly concentrated and absorbent samples. Because of these characteristics, fiber-optical sensors appear suitable for use in the monitoring and control of production processes. The measuring principle of fiber-optical quasi-elastic light scattering (FOQELS) makes use of the Doppler shift of laser light which has been scattered by moving scattering centers. For applications in velocimetry, the particle movement is due to flow. When used to determine diffusion coefficients and hence particle diameters, on the other hand, the particle movement is due to Brownian molecular movement.

The industrial implementation of an approriate measuring system using a fiber-optical sensor is known and is described in the literature (Applied Optics 14 (1975), 189). In this apparatus, the laser light is guided to a fiber-optical probe via a beam divider. Some of the light scattered back by the scattering medium is reflected by the same beam divider to a photodetector. In this way, not less than 75% of the available light intensity are lost.

This intensity loss is reduced if, instead of a beam divider, a fully reflecting mirror is used, in the middle of which a hole is drilled (Microwaves, Optics and Acoustics 2 (1978), 13). The laser beam passes unattentuated through the mirror, via this hole, and is focused on a fiber-optical probe. The light reflected back by the scattering medium emerges from the fiber-optical probe and is then collimated by the focusing lens at the angle determined by the numerical aperture of the light guide and illuminates a relatively large area of the mirror. Thus, a large percentage of the scattered light is reflected to the photodetector. Depending on the dimensions, the losses are only 5-10% of the light intensity.

In the measuring principle described, quantitative determination of the Doppler shift of the scattered light is carried out by heterodyne detection, since a superposition of scattered, Doppler-shifted light and unshifted laser light is recorded at the photodetector. The unshifted laser light is due to reflections at the end of the fiber-optical immersion probe and to Rayleigh scattering at defects in the light guide. Electronic recording of the heterodyne fluctuating signal is effected alternatively by frequency analysis or autocorrelation analysis. The flow velocities and the diffusion coefficients can be determined from the measured frequency distribution curve or autocorrelation function. For monodisperse, spherical and noninteracting particles, for example, the relationship between the decay constant $\gamma$ of the autocorrelation function, which is identical to the half width of the Lorentz-type frequency distribution, and the diffusion coefficient D is given by $\gamma = DK^2$, where K is the scattering vector.

In the evaluation of the measured results, it should be noted that the geometry corresponds to 180° scattering. This means that, for polydisperse samples, a mean diffusion coefficient of the form $$D_{180°} = \frac{\Sigma_i N_i M_i^2 P(180°, M_i) D}{\Sigma_i N_i M_i^2 P(180°, M_i)}$$

where $N_i$ is the number, $M_i$ the mass, $D_i$ the diffusion coefficient and $P(180°, M_i)$ the scattering function of the particles of the i th component of the polydisperse distribution, From this, using the Stokes-Einstein relationship $$d_{180°} = \frac{kT}{3\pi\eta D_{180°}}$$

it is possible to calculate the associated hydrodynamic, equivalent spherical particle diameter $d_{180°}$. Here, k is the Boltzmann constant, T the temperature and $\mu$ the viscosity of the solvent.

Some disadvantages of the stated measuring method have recently been overcome (U.S. Pat. No. 4,637,716) by a method in which coherent laser light is passed via a fiber-optical coupler to a fiber-optical sensor which dips into the scattering medium as an immersion probe, and the light scattered back by the scattering medium is picked up by the same fiber-optical sensor, branched by the fiber-optical coupler and passed to a photodetector. In the prior art, the emergence surface for the laser light is at the end of the sensor, at right angles to the longitudinal axis of the light guide fiber.

The set-up of the fiber-optical measuring method is further simplified and improved if the laser used is an integrated semiconductor laser and the laser light is passed directly via a light guide to the fiber-optical coupler; if the photodetector used is an integrated detector, for example a silicon avalanche photodiode and the scattered light branched by the fiber-optical coupler is passed directly via a light guide to the detector; if the optical set-up is fully integrated, and if the fiber-optical immersion probe consists of a light guide which is terminated by an end sleeve and additionally surrounded by a protective tube and furthermore has been rendered hydrophobic at the emergence surface for the laser light.

The advantages obtained by this prior art are in particular that, instead of a discrete set-up consisting of individual, precisely positioned optical components, a partially or completely integrated optical set-up is employed, so that the path of the laser light and of the scattered light passes substantially or completely through light guides and fiber-optical components. This dispenses with all discrete optical components, as well as the requirement for interferometric stability of the set-up.

The arrangement can be operated anywhere since it need no longer be set up on an optical bench. The fiber-optical components are merely connected to one another by appropriate plug connectors. Moreover, the measurement can be carried out at inaccessible points since the fiber-optical immersion probe is flexible and can be of considerable length.

By using fiber-optical components conventionally employed in communication engineering, handling of the fiber-optical quasi-elastic light scattering (FOQELS) is very greatly faacilitated. This opens up many novel potential applications in velocimetry and in the measurement of diffusion coefficients in research and industry.

However, a significant disadvantage of the measuring technique described above is that measurements can only be carried out on systems having a high concentration of scattering centers. Thus, measurements on latex dispersions were possible only in a concentration range $\geq 1\%$ (U.S. Pat. No. 4,637,716). The fiber-optical version of quasi-elastic light scattering (FOQELS) thus opens up a wide concentration range for characterization of disperse systems by measurements by QELS, since the standard version of QELS requires highly dilute systems, and thus constitutes a considerable technical advance.

There is however also considerable interest in the characterization of dilute disperse systems by means of an immersion probe, since the standard version of QELS requires transfer of the sample to a measuring cell specific to the apparatus, which, owing to the necessary manipulations and the size of the sample volume required, makes the measuring method difficult or even impossible to use in many cases in the industrial and biological sectors. Such tasks arise in all in situ measurements when only small particle concentrations are available, for example in fiber-optical laser Doppler anemometry with tracer particle concentrations $<<1\%$ or in the measurement of nucleation/growth kinetics at the beginning of the precipitation reaction in a crystallization reactor. In the biological/medical sector, the characterization of an immunological agglutination reaction, which, for example, can be detected by the agglomeration of antigen-modified or anti-body-modified latex particles, by FOQELS at low antigen-/antibody concentration and with a sample volume in the $\mu l$ range is of great interest.

It is an object of the present invention to provide a fiber-optical sensor which, even at particle concentrations of $<1\%$ by volume, permits the in situ measurement of the diffusion coefficient of these scattering centers by QELS and, if required, allows such measurements to be carried out for a sample volume in the $\mu l$ range.

We have found that this object is achieved, according to the invention, by the defining feature of the claim.

An embodiment of the invention is illustrated in FIG. 1. Using a prior art optoelectronic FOQELS set-up 1, laser light is passed from the light source 2 via a light guide 3 and a coupler 4 to the sensor 6 which is in the form of an immersion probe and is terminated by an end sleeve 5, the light leaving the said sensor through the fiber end surface 7 inclined at an angle $\phi$, the angle of inclination $\phi$ being formed by the optical axis 8 of the light guide fiber 3 and the normal 9 of the emergence surface.

The light scattered back by the sample 10 passes via the fiber end surface and back into the light guide 3 and, after being divided in the coupler 4, passes via a light guide 11 to a detector 12 having associated signal processing electronics.

While the FOQELS version using a prior art fiber-optical sensor (i.e. $\phi = 0°$, does not permit measurements at particle concentrations of $<1\%$ by weight, since no correlation function is obtained after analysis of the back-scattered light in 12, it is very surprising that, at an angle of inclination of $\phi > 1°$, a correlation function is recorded for the same sample even at 100-fold dilution, from which correlation function it is possible to determine the diffusion coefficient and, via the Strokes-Einstein relationship, the particle diameter.

Figure 2:
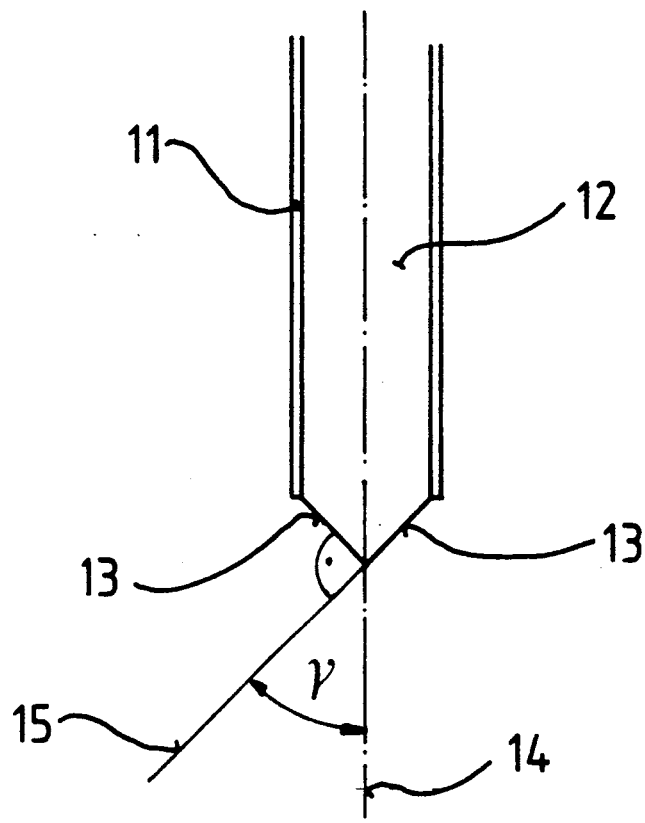

Another embodiment of the invention is shown in FIG. 2. The laser light passed to the sensor 12 via the light guide 3, as shown in FIG. 1, leaves the sensor 12, in the form of an immersion probe and terminated by an end sleeve 11, via the fiber end surface 13 which is roof-shaped with an angle of inclination $\gamma$, the angle of inclination $\gamma$ being defined by the optical axis 14 of the light guide 3 and the normal 15 of the roof-shaped emergence surface.

Figure 3:
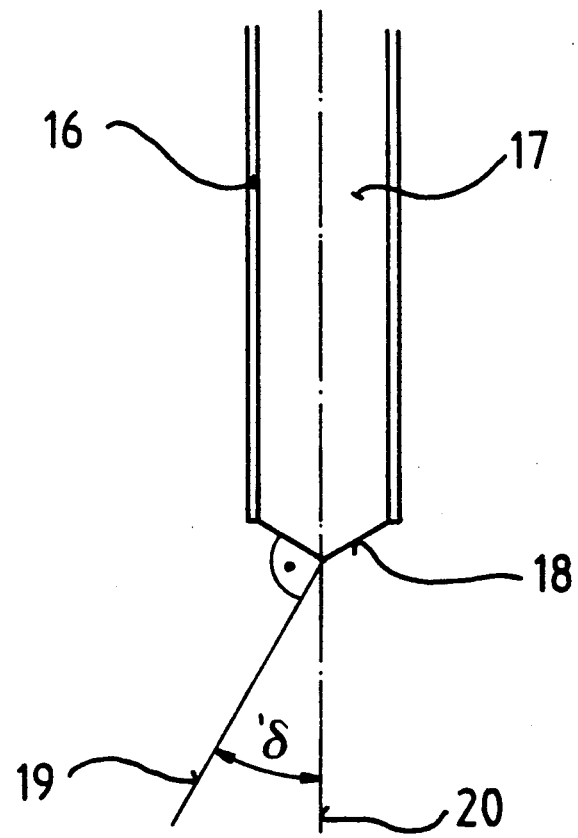

Another embodiment of the invention is shown in FIG. 3. The laser light leaves the sensor 17 terminated by an end sleeve 16 through the conical end surface 18 having an angle of inclination $\delta$. The angle of inclination $\delta$ is defined by the normal to the lateral surface 19 of the cone and the optical axis of the light guide 20.

Figure 4:
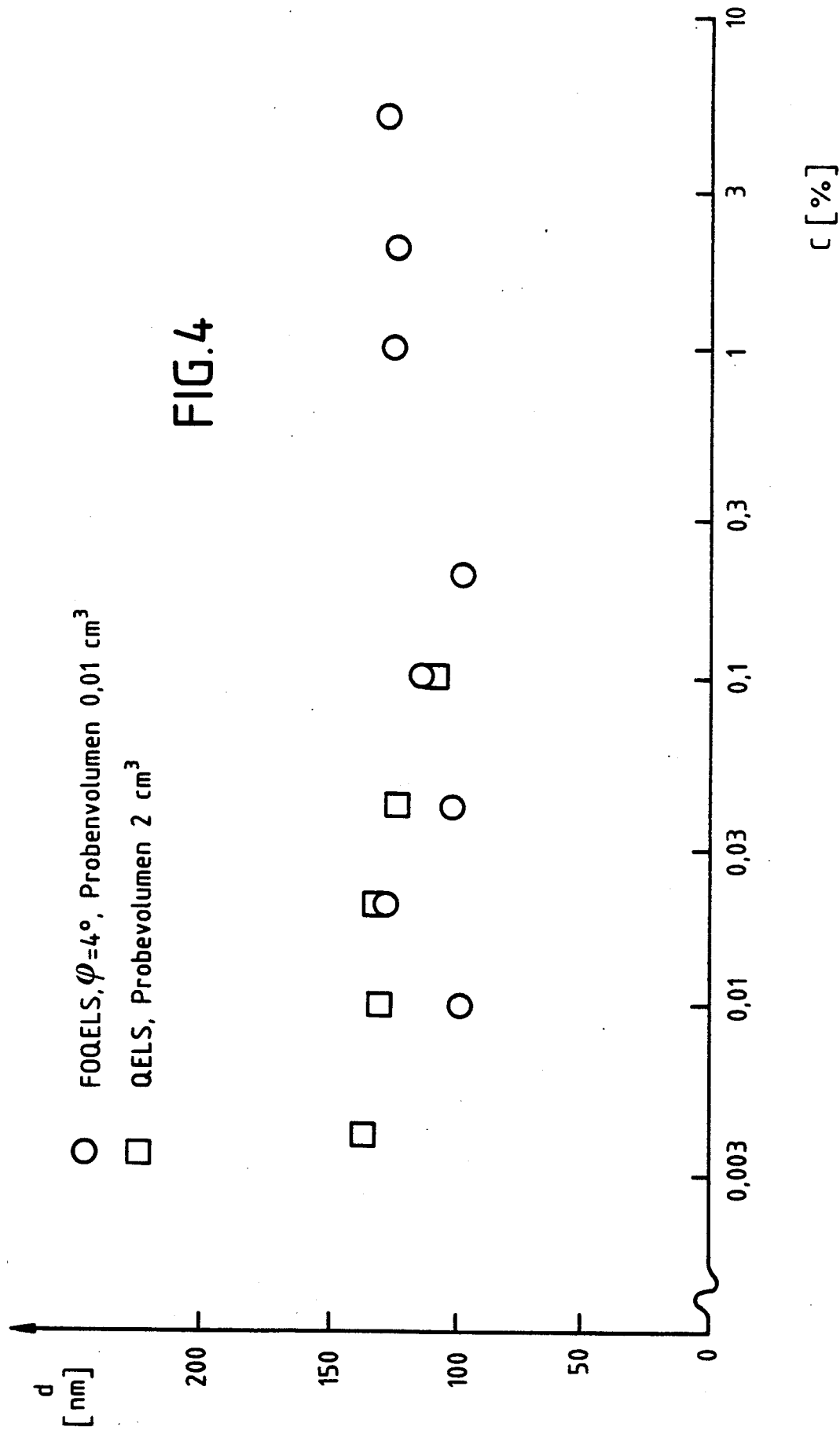

FIG. 4 shows, as a typical measurement result, the particle diameter of a latex sample for variation of the solids concentration over three powers of ten, from 0.01 to 10% by weight, the measuring arrangement described in FIG. 1 being used. The measurements were carried out using a multimode fiber, the angle of inclination $\phi$ of the fiber end surface at the sensor being 4°. In comparison with the measured results obtained by a fiber-optical method, a few measured points obtained by conventional QELS using a measuring cell with a path length of 1 cm are also plotted. In the concentration range from 0.01 to 0.1% by weight, where measurements are possible both by conventional QELS and by the novel version of FOQELS, good agreement between the measured results is found. However, a cell volume of 2 cm$^3$ is required to carry out the QELS measurement, whereas a sample volume of only 0.01 cm$^3$ is necessary for the FOQELS measurement.

Figure 5:
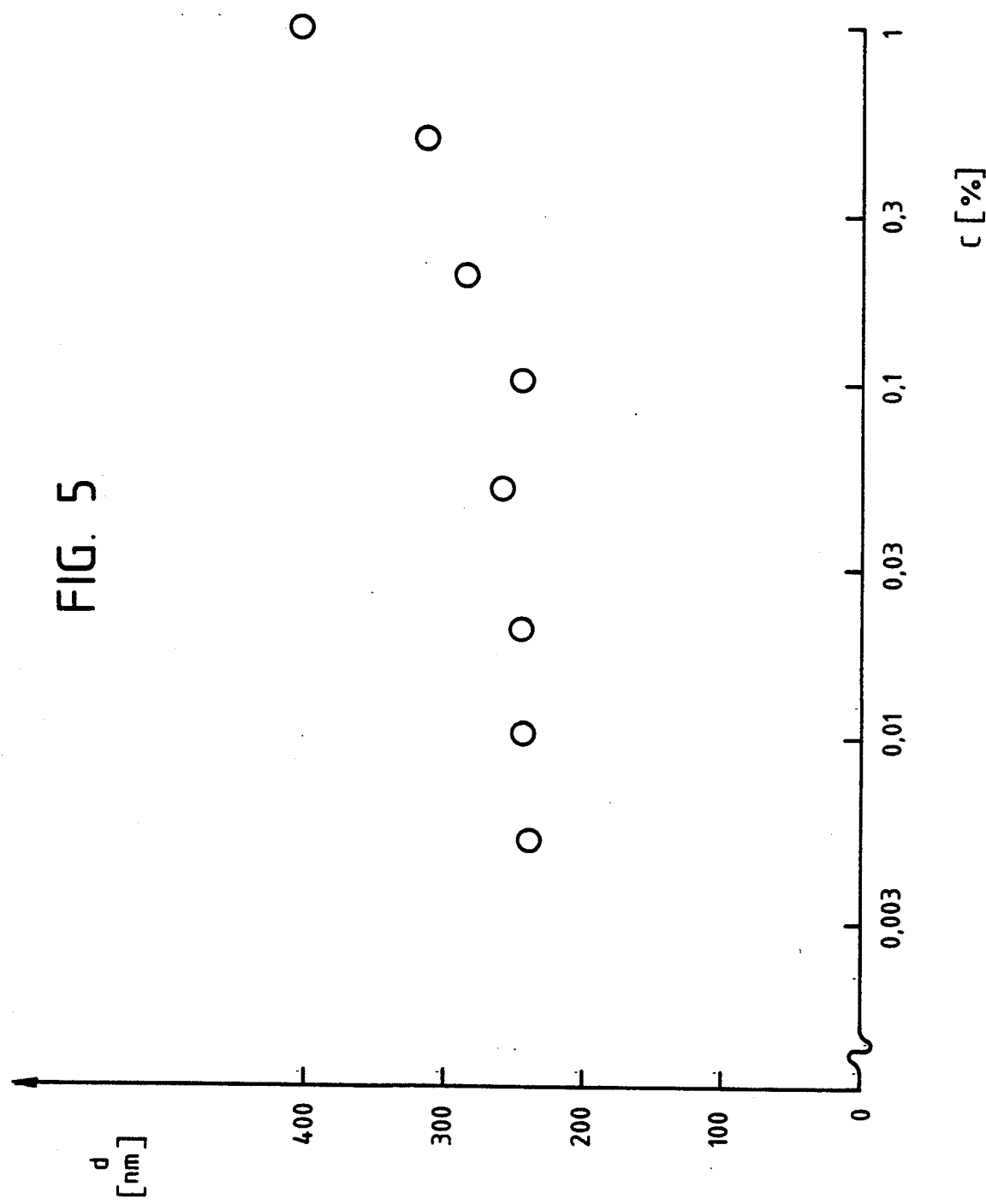

FIG. 5 shows the result of a particle size measurement according to FIG. 1 for a dilution series of a micronized $\beta$-carotene using a single-mode fiber, the angle of inclination $\phi$ of the fiber end surface at the sensor being about 2°. At concentrations c $>1\%$, deviations from the actual particle diameter are observed since the free diffusion of particles is hindered by interaction between them. In this system, measurements are possible even at c = 0.005%. The sample volume required for the measurement is only a few $\mu l$ with a fiber diameter of 5 $\mu m$.

Figure 6:
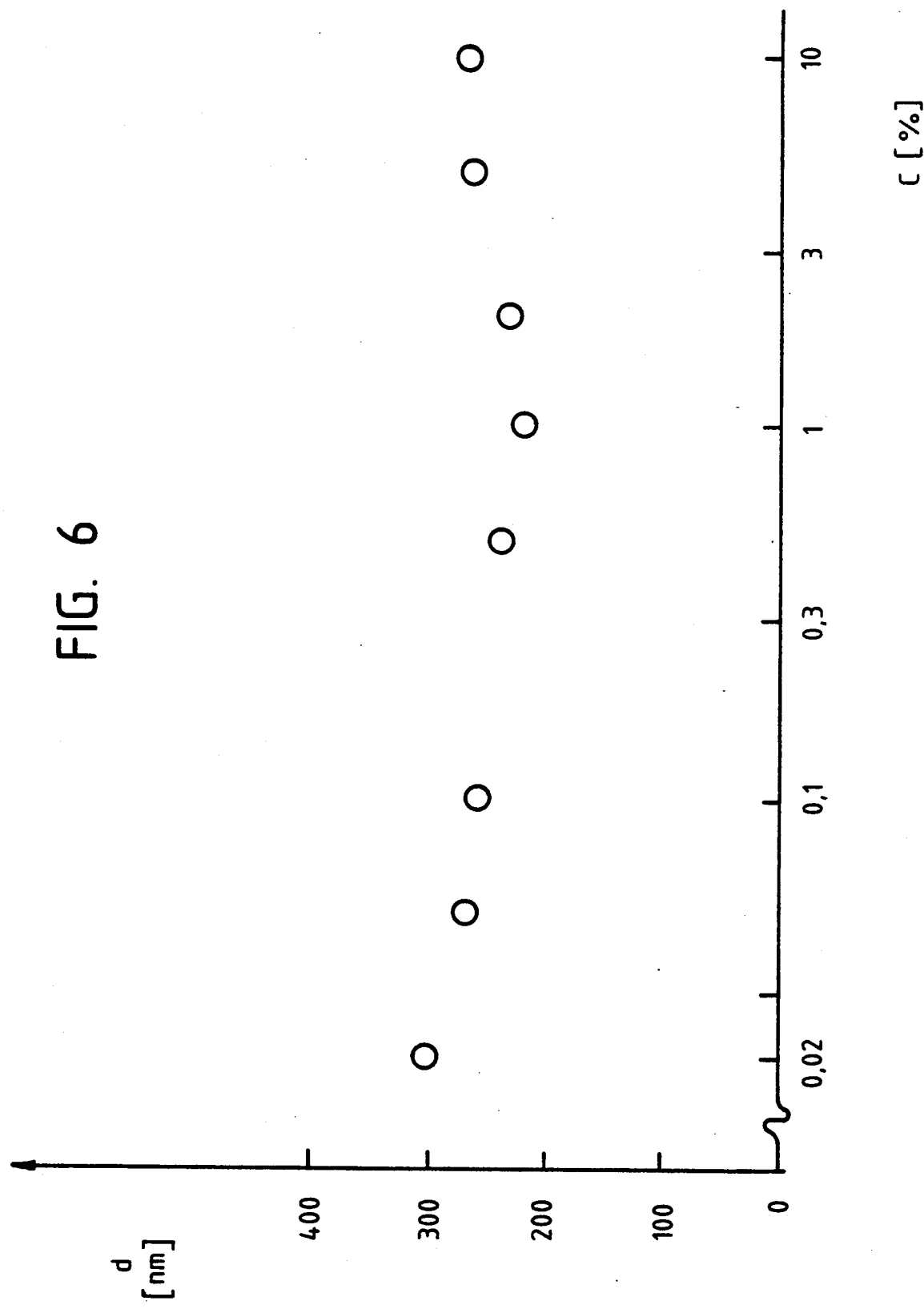

FIG. 6 shows the result of the particle diameter measurement according to FIG. 1 for a dilution series of a latex sample in the concentration range from 0.02 to 10%, using a single-mode fiber, the angle of inclination of the fiber end surface at the sensor being 4°.

We claim:

1. A fiber-optical sensor for measuring the Doppler broadening of scattered laser light by the principle of quasi-elastic light scattering (QELS), the scattered light originating from scattering of laser light by particles in movement in the sample (10) being measured, having a light guide (3) selected from the group consisting of a single-mode light guide and a multi-mode light guide used as an immersion probe into said sample and which transfers laser light from a source (2) to said sample and further which transfers light scattered from said sample to a detector (12) wherein the emergence surface (7) for the laser light at the end of said light guide is inclined at an angle $1° \leqq \phi \leqq 15°$, the angle of inclination being defined by the optical axis (8) of said light guide and the normal (9) of said emergence surface.

2. A fiber-optical sensor as defined in claim 1, wherein the emergence surface is inclined at an angle of $1° \leqq \phi \leqq 6°$.

* * * * *